United States Patent
Lee et al.

(10) Patent No.: US 11,430,360 B2
(45) Date of Patent: Aug. 30, 2022

(54) ELECTRONIC DEVICE

(71) Applicant: Samsung Display Co., Ltd., Gyeonggi-do (KR)

(72) Inventors: Hyeon Jun Lee, Seoul (KR); Chul Kim, Hwaseong-si (KR); Hee Seomoon, Seoul (KR); Taehee Lee, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/377,382

(22) Filed: Jul. 16, 2021

(65) Prior Publication Data

US 2022/0130305 A1    Apr. 28, 2022

(30) Foreign Application Priority Data

Oct. 27, 2020  (KR) ................. 10-2020-0140679

(51) Int. Cl.
| | |
|---|---|
| *G09G 3/16* | (2006.01) |
| *G06F 3/041* | (2006.01) |
| *A61B 5/024* | (2006.01) |
| *H04N 5/33* | (2006.01) |
| *H01L 31/09* | (2006.01) |

(52) U.S. Cl.
CPC ........... *G09G 3/16* (2013.01); *A61B 5/02433* (2013.01); *G06F 3/0412* (2013.01); *H01L 31/09* (2013.01); *H04N 5/33* (2013.01); *G06F 2203/04105* (2013.01); *G09G 2300/0439* (2013.01); *G09G 2310/0264* (2013.01); *G09G 2360/14* (2013.01); *G09G 2380/08* (2013.01)

(58) Field of Classification Search
CPC .. G06F 3/0412; G06F 3/0443; G06F 3/04184; G06F 3/0445; G06F 3/044; G06F 2203/04105; G06F 3/04182; G06F 3/0447; G06F 1/3218; G06F 21/32; G06V 40/13; G06V 40/67; G06V 40/70; H01L 27/30; H01L 27/32; H01L 27/3206; H01L 27/3211; H01L 27/3225; H01L 27/3237; H01L 27/3241

See application file for complete search history.

(56) References Cited

U.S. PATENT DOCUMENTS

| | | |
|---|---|---|
| 9,049,998 B2 | 6/2015 | Brumback et al. |
| 10,231,674 B2 | 3/2019 | Newberry |
| (Continued) | | |

FOREIGN PATENT DOCUMENTS

| | | |
|---|---|---|
| KR | 10-2018-0067196 | 6/2018 |
| KR | 10-2019-0041648 | 4/2019 |

*Primary Examiner* — Sanjiv D. Patel
(74) *Attorney, Agent, or Firm* — H.C. Park & Associates, PLC

(57) ABSTRACT

An electronic device includes: a display module including a display panel and an input sensor disposed on the display panel, the display panel having a first area including a plurality of pixels and a second area having a transmittance higher than that of the first area; a first sensor disposed below the display module, overlapping the second area, and configured to measure a first signal having biometric information of a user; a second sensor disposed to surround the first sensor, overlapping the first area, and configured to measure a second signal applied from the user; and a driving unit connected to the display module, the first sensor, and the second sensor, the driving unit configured to drive the first sensor and the second sensor together with the display module.

20 Claims, 12 Drawing Sheets

(56) References Cited

U.S. PATENT DOCUMENTS

| | | |
|---|---|---|
| 10,552,696 B2 | 2/2020 | Cho et al. |
| 10,885,301 B2 | 1/2021 | Cho et al. |
| 2014/0092064 A1 | 4/2014 | Bernstein et al. |
| 2017/0086686 A1 | 3/2017 | Narasimhan et al. | ically
ELECTRONIC DEVICE

CROSS-REFERENCE TO RELATED APPLICATION

This application claims priority from and the benefit of Korean Patent Application No. 10-2020-0140679, filed on Oct. 27, 2020, which is hereby incorporated by reference for all purposes as if fully set forth herein.

BACKGROUND

Field

Embodiments of the invention relate generally to an electronic device, and more specifically, to an electronic device including a biometric information sensor.

Discussion of the Background

The development of electronic devices such as portable terminals having new functions is being carried out at a rapid pace. Recently, portable terminals are not only for playing a role as a display device that outputs images or information as a smart device, but also for playing various roles as an electronic device with various functions for the user's convenience.

The above information disclosed in this Background section is only for understanding of the background of the inventive concepts, and, therefore, it may contain information that does not constitute prior art.

SUMMARY

Electronic devices constructed according to the principles of the invention are capable of measuring biometric information of a user by using a first sensor and a second sensor of the electronic devices. For example, the electronic devices include an integrated driving unit that is formed by integrating driving units for driving the first sensor and the second sensor and a driving unit for driving a display module of the electronic devices.

Additional features of the inventive concepts will be set forth in the description which follows, and in part will be apparent from the description, or may be learned by practice of the inventive concepts.

According to an aspect of the invention, an electronic device includes: a display module including a display panel and an input sensor disposed on the display panel, the display panel having a first area including a plurality of pixels and a second area having a transmittance higher than that of the first area; a first sensor disposed below the display module, overlapping the second area, and configured to measure a first signal having biometric information of a user; a second sensor disposed to surround the first sensor, overlapping the first area, and configured to measure a second signal applied from the user; and a driving unit connected to the display module, the first sensor, and the second sensor, the driving unit configured to drive the first sensor and the second sensor together with the display module.

The second area of the display panel may include a plurality of light emitting areas, and a plurality of signal transmission areas adjacent to the plurality of light emitting areas.

The electronic device may further include a main circuit board for driving the display module, wherein the driving unit may be disposed on the main circuit board.

The driving unit may include: a display panel driver configured to drive the display panel; an input sensor driver configured to drive the input sensor; a first sensor driver configured to drive the first sensor; and a second sensor driver configured to drive the second sensor.

The driving unit may further include a biometric information calculator configured to calculate the biometric information of the user based on the first signal measured from the first sensor driver and the second signal measured by the second sensor driver.

The first sensor may be a photoplethysmography (PPG) sensor and may be configured to measure at least one of a user's blood pressure, oxygen saturation, and heart rate.

The first sensor may include a light emitter for providing light and a light receiver for detecting light reflected from the user, wherein the light emitter may include at least one of an infrared light source for emitting infrared light and a red light source for emitting red light, wherein the light receiver may be a photodiode or a camera module.

The first sensor may include a sensor driving module for driving the light receiver and the light emitter.

The light receiver may be formed in the sensor driving module.

The sensor driving module may be connected to the driving unit, wherein the driving unit may be configured to drive the first sensor through the sensor driving module, and configured to directly drive the second sensor.

The electronic device may further include a plurality of signal wirings electrically connecting the first sensor and the second sensor to the driving unit.

The plurality of signal wirings may include a plurality of first signal wirings electrically connected to the first sensor and a plurality of second signal wirings electrically connected to the second sensor.

According to another aspect of the invention, an electronic device includes: a display module including a display panel and an input sensor disposed on the display panel, the display panel having a first area including a plurality of pixels and a second area having a transmittance higher than that of the first area; a first sensor disposed below the display module, overlapping the second area, and configured to measure a first signal having biometric information of a user; a second sensor disposed to surround the first sensor, overlapping the first area, and configured to measure a second signal applied from the user; a sensor driving module disposed on the first sensor, connected to the second sensor, and configured to drive the first sensor and the second sensor; and a driving unit connected to the display module and the sensor driving module, the driving unit configured to drive the display module and the sensor driving module.

The sensor driving module may alternately drive the first sensor and the second sensor.

The electronic device may further include a plurality of first signal wirings electrically connecting the second sensor to the sensor driving module.

The electronic device may further include a plurality of second signal wirings electrically connecting the sensor driving module to the driving unit.

The sensor driving module may be an analog front end for converting the first signal and the second signal into a driving signal.

The driving unit may include a biometric information calculator configured to receive the driving signal from the sensor driving module and calculate biometric information of the user based on the driving signal.

The first sensor may include a light emitter for providing light and a light receiver for detecting reflected light, wherein the light emitter may include at least one of an infrared light source for emitting infrared light and a red light source for emitting red light, wherein the light receiver may be a photodiode or a camera module.

The first sensor may include a photoplethysmography (PPG) sensor for measuring a change in blood flow by optically detecting light reflected or transmitted from the user's tissue and blood, and obtaining heart rate, blood pressure, respiration, and blood oxygen saturation, wherein the second sensor may include a pressure sensor.

It is to be understood that both the foregoing general description and the following detailed description are exemplary and explanatory and are intended to provide further explanation of the invention as claimed.

BRIEF DESCRIPTION OF THE FIGURES

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
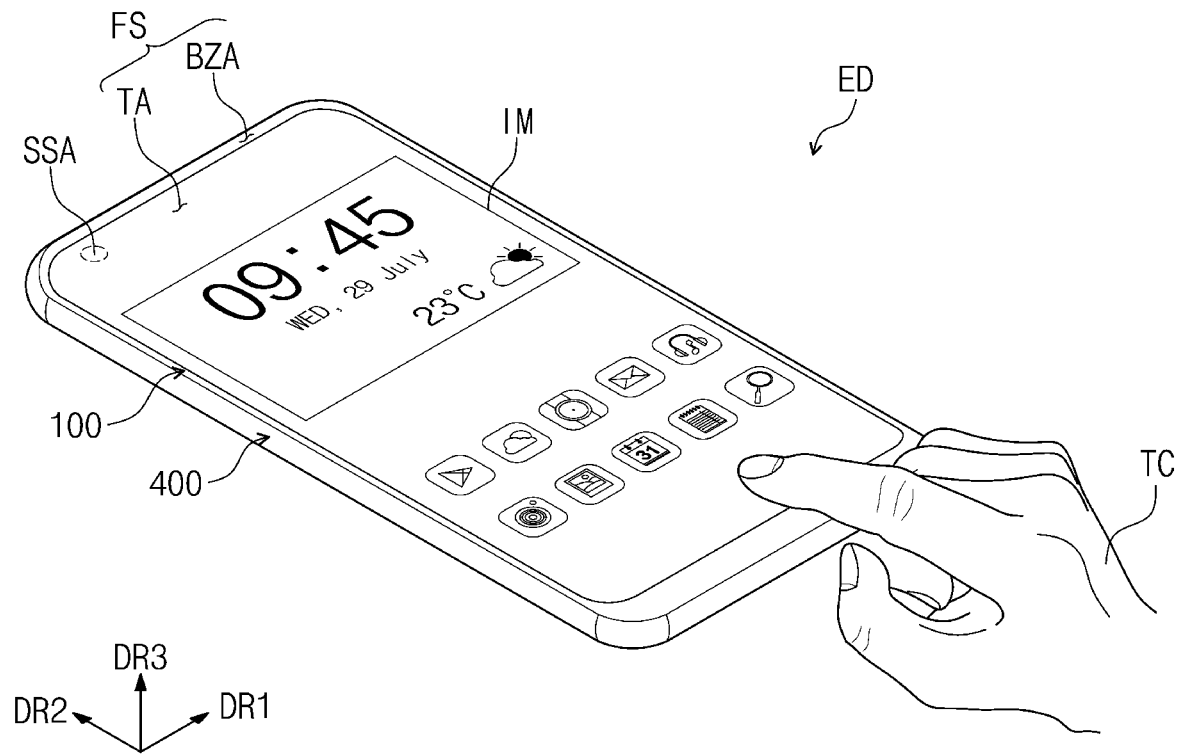
FIG. 1 is a perspective view of an embodiment of an electronic device constructed according to the principles of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the DR1-axis, the DR2-axis, and the DR3-axis are not limited to three axes of a rectangular coordinate system, such as the x, y, and z-axes, and may be interpreted in a broader sense. For example, the DR1-axis, the DR2-axis, and the DR3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, embodiments of the inventive concepts will be described with reference to the drawings.

Figure 2:
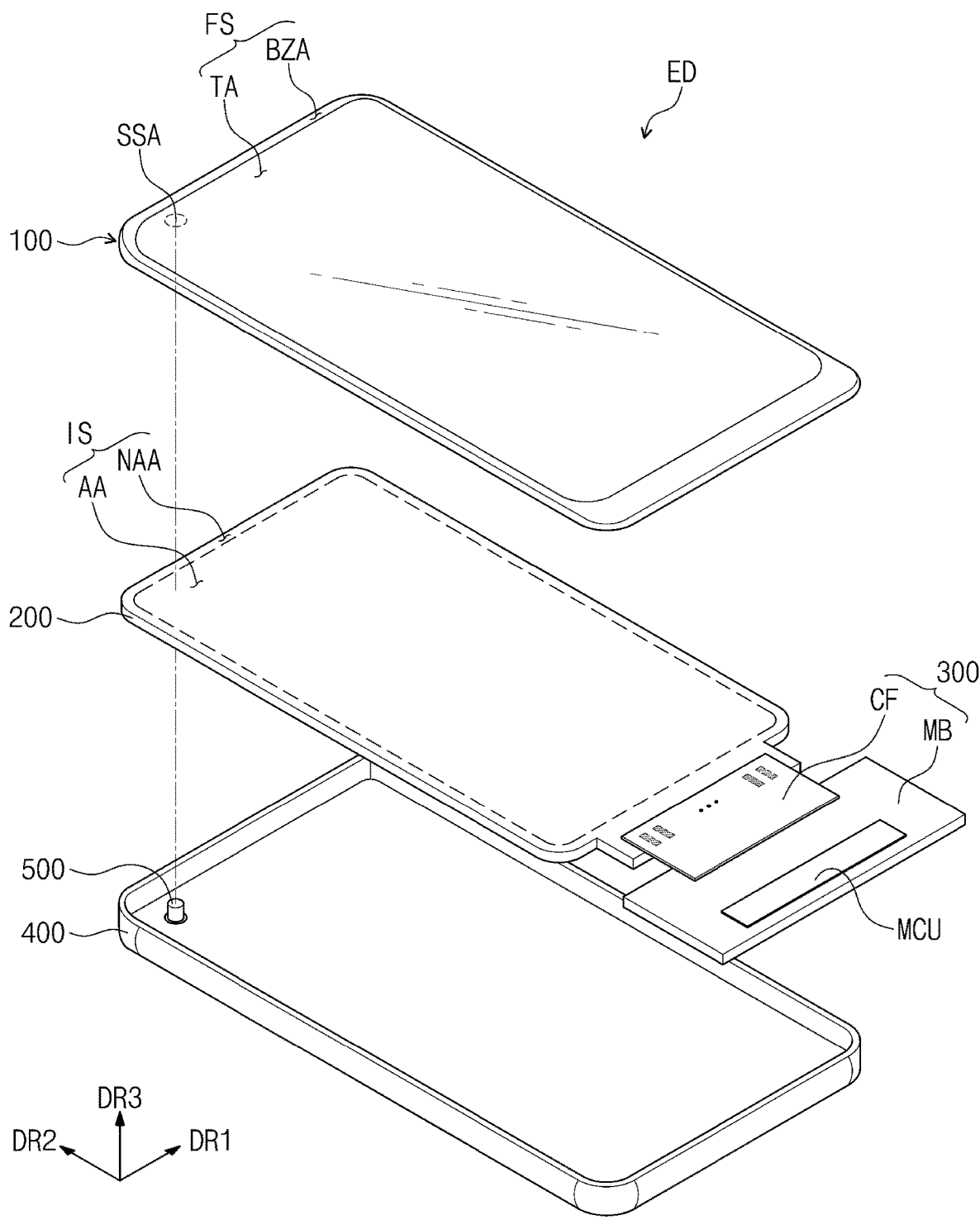
FIG. 2 is an exploded perspective view of the electronic device of FIG. 1.

FIG. 1 is a perspective view of an electronic device according to an embodiment, and FIG. 2 is an exploded perspective view of an electronic device according to an embodiment.

Referring to FIGS. 1 and 2, an electronic device ED may be a device activated according to an electrical signal. The electronic device ED may include various embodiments. For example, an electronic device ED may be applied to small and medium-sized electronic devices (e.g., personal computers, notebook computers, personal digital terminals, car navigation units, game machines, portable electronic devices, and cameras) and large electronic devices (e.g., televisions, monitors, or external billboards). In addition, these are presented only as examples, and may be employed in other electronic devices. In an embodiment, the electronic device ED is exemplarily illustrated as a smart phone.

The electronic device ED may display the image IM toward the third direction DR3 on the display surface FS parallel to each of the first and second directions DR1 and DR2. The display surface FS, on which the image IM is displayed, may correspond to the front surface of the electronic device ED and may correspond to the front surface FS of the window 100. Hereinafter, the same reference numerals may be used for the display surface and the front surface of the electronic device ED, and the front surface of the window 100. The image IM may include a still image as well as a dynamic image (e.g., a video). In FIG. 1, a clock window and application icons are illustrated as an example of an image IM.

In an embodiment, the front surface (or upper surface) and the rear surface (or lower surface) of each member may be defined based on the direction in which the image IM is displayed. The front and rear surfaces are opposing to each other in the third direction DR3, and a normal direction of each of the front and rear surfaces may be parallel to the third direction DR3. The third direction DR3 may be a direction intersecting the first direction DR1 and the second direction DR2. The first direction DR1, the second direction DR2, and the third direction DR3 may be orthogonal to each other.

In the descriptions, a plane defined by the first direction DR1 and the second direction DR2 is defined as a plane, and the expression "when viewed in plane or on a plane" or "in plan view" may be defined as being viewed in the third direction DR3.

The electronic device ED may include a window 100, a display module 200, a driving circuit unit 300, a housing 400, and an electronic module 500. In an embodiment, the window 100 and the housing 400 may be combined to form the exterior of the electronic device ED.

The window 100 may include an optically transparent insulating material. For example, the window 100 may include glass or plastic. The window 100 may have a multilayer structure or a single layer structure. For example, the window 100 may include a plurality of plastic films bonded with an adhesive, or may include a glass substrate and a plastic film bonded with an adhesive.

When viewed in plane, the window 100 may be divided into a transmission area TA and a bezel area BZA. The transmission area TA may be an optically transparent area. The bezel area BZA may be an area having relatively low light transmittance, as compared to the transmission area TA. The bezel area BZA may define the shape of the transmission area TA. The bezel area BZA is adjacent to the transmission area TA, and may surround the transmission area TA.

The bezel area BZA may have a predetermined color. The bezel area BZA may cover the peripheral area NAA of the display module 200 to prevent the peripheral area NAA from being visually recognized from the outside. For example, this is illustrated by way of example, and in the window 100 according to an embodiment, the bezel area BZA may be omitted.

In an embodiment, the sensing area SSA may overlap the electronic module 500, e.g., in the third direction DR3. The electronic device ED may receive an external signal required for the electronic module 500 through the sensing area SSA or may provide a signal outputted from the electronic module 500 to the outside. According to an embodiment, the sensing area SSA may be defined to overlap the transmission area TA. Accordingly, a separate area provided to provide the sensing area SSA in an area other than the transmission area TA may be omitted. Accordingly, the area of the bezel area BZA may be reduced.

FIGS. 1 and 2 illustrate that there is only one sensing area SSA, but embodiments are not limited thereto. For example, the sensing area SSA may include two or more sensing areas. In addition, in FIGS. 1 and 2, the sensing area SSA is defined at the upper left of the transmission area TA, but embodiments are not limited thereto. For example, the sensing area SSA may be defined in various areas such as the upper right of the transmission area TA, the center of the transmission area TA, the lower left of the transmission area TA, or the lower right of the transmission area TA.

The display module 200 may be disposed under the window 100. The display module 200 may display an image IM. The display module 200 may include a front surface IS including an active area AA and a peripheral area NAA. The active area AA may be an area activated according to an electrical signal.

In an embodiment, the active area AA may be an area in which an image IM is displayed. The transmission area TA may overlap the active area AA. For example, the transmission area TA may overlap the entire surface or at least a part of the active area AA, e.g., in the third direction DR3. Accordingly, the user may visually recognize the image IM through the transmission area TA.

The peripheral area NAA may be an area covered by the bezel area BZA. The peripheral area NAA may be adjacent to the active area AA. The peripheral area NAA may surround the active area AA. A driving circuit or a driving wiring for driving the active area AA may be disposed in the peripheral area NAA.

In an embodiment, the display module 200 is assembled in a flat state with the active area AA and the peripheral area NAA facing the window 100. However, this is illustrated by way of example, and a part of the peripheral area NAA may be curved. In this case, a part of the peripheral area NAA faces the rear surface of the electronic device ED, so that the area of the bezel area BZA in the front surface of the electronic device ED may be reduced. Alternatively, the display module 200 may be assembled with a portion of the active area AA, which is bent. Alternatively, in the display module 200 according to an embodiment, the peripheral area NAA may be omitted.

The driving circuit unit 300 may be electrically connected to the display module 200. The driving circuit unit 300 may include a main circuit board MB and a flexible film CF.

The flexible film CF may be electrically connected to the display module 200. The flexible film CF may be connected to pads of the display module 200 disposed in the peripheral area NAA. The flexible film CF may provide an electrical signal for driving the display module 200 to the display module 200. The electrical signal may be generated from the flexible film CF or may be generated from the main circuit board MB. The main circuit board MB may include various driving circuits for driving the display module 200 or a connector for supplying power. In an embodiment, the main circuit board MB may include a driving unit MCU. The driving unit MCU may include driving circuits for driving the display panel 210 and the input sensor 220. The driving unit MCU may include driving circuits for driving the electronic module 500. A detailed description will be given later.

In an embodiment, an area of the display module 200 corresponding to the sensing area SSA may have a relatively higher transmittance than the active area AA that does not overlap the sensing area SSA. For example, at least some of the components of the display module 200 may be removed. Accordingly, the electronic module 500 may easily transmit and/or receive a signal through the sensing area SSA.

The electronic module 500 may be disposed under the display module 200. Specifically, the electronic module 500 may be disposed under the display panel. When viewed in plane, the electronic module 500 may overlap the sensing area SSA. The electronic module 500 may receive an external input transmitted through the sensing area SSA or may provide an output through the sensing area SSA. The electronic module 500 may include a camera module and related electronic components. The camera module may include a camera, an infrared sensor, and various sensors including a proximity sensor. In an embodiment, the electronic module 500 may include a biometric sensor and a pressure sensor.

The housing 400 may be coupled to the window 100. The housing 400 may be combined with the window 100 to provide an inner space. The display module 200 and the electronic module 500 may be accommodated in the inner space.

The housing 400 may include a material having relatively high rigidity. For example, the housing 400 may include a plurality of frames and/or plates made of glass, plastic, or metal, or a combination thereof. The housing 400 may stably protect the components of the electronic device ED accommodated in the inner space from external impact.

Figure 3:
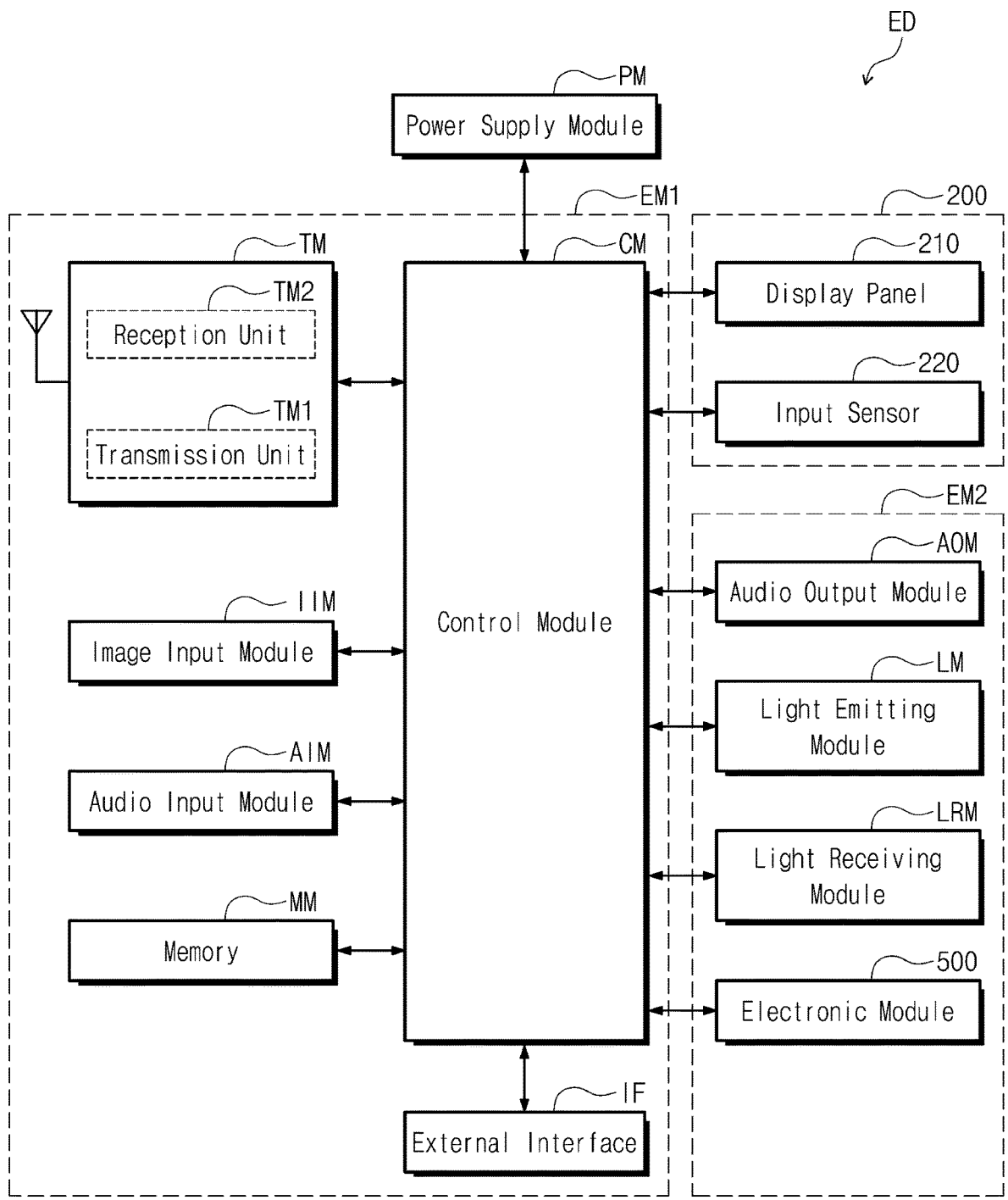
FIG. 3 is a block diagram of the electronic device of FIG. 1.

FIG. 3 is a block diagram of an electronic device according to an embodiment.

Referring to FIG. 3, the electronic device ED may include a display module 200, a power supply module PM, a first electronic module EM1, and a second electronic module EM2. The display module 200, the power supply module PM, the first electronic module EM1, and the second electronic module EM2 may be electrically connected to each other.

The display module 200 may include a display panel 210 and an input sensor 220.

The display panel 210 may be a component that substantially generates an image IM. The image IM generated by the display panel 210 is displayed on the front surface IS and is visually recognized by the user from the outside through the transmission area TA.

The input sensor 220 senses an external input TC applied from the outside. For example, the input sensor 220 may detect an external input TC provided to the window 100. The external input TC may be a user's input. The user's input includes various types of external inputs such as the user's body, light, heat, pen, pressure, or the like. In an embodiment, the external input TC is shown by the user's hand applied to the front surface FS. However, embodiments are not limited thereto. For example, as described above, the external input TC may be provided in various forms. In addition, according to the structure of the electronic device ED, an external input TC applied to the side or rear surface of the electronic device ED may be detected, but embodiments are not limited thereto.

The power supply module PM supplies power necessary for the overall operation of the electronic device ED. The power supply module PM may include a conventional battery module.

The first electronic module EM1 and the second electronic module EM2 may include various functional modules for operating the electronic device ED.

The first electronic module EM1 may be directly mounted on a motherboard electrically connected to the display module 200. Alternatively, the first electronic module EM1 may be mounted on a separate board and electrically connected to the motherboard through a connector.

The first electronic module EM1 may include a control module CM, a wireless communication module TM, an image input module IIM, an audio input module AIM, a memory MM, and an external interface IF. Some of the modules are not mounted on the motherboard, but may be electrically connected to the motherboard through a flexible circuit board.

The control module CM controls the overall operation of the electronic device ED. The control module CM may be a microprocessor. For example, the control module CM activates or deactivates the display module 200. The control module CM may control other modules such as an image input module IIM or an audio input module AIM based on a touch signal received from the display module 200.

The control module CM may be a microprocessor that is connected to the electronic module 500 and controls the operation of the electronic module 500. In an embodiment, the control module CM may control the overall operation of the electronic module 500. The control module CM may include a processor that controls the electronic module 500. For example, the control module CM may perform an algorithm for converting and regenerating signals related to the user's biometric information measured through the electronic module 500. For example, the control module CM may include a driving unit MCU that drives the electronic module 500 including a biometric sensor and a pressure sensor. This will be described later.

The wireless communication module TM may transmit wireless signals to other terminals and/or receive the wireless signals from the other terminals using a Bluetooth or Wi-Fi line. The wireless communication module TM may transmit and/or receive voice signals using a general communication line. The wireless communication module TM may include a transmission unit TM1 that modulates and transmits a signal to be transmitted, and a reception unit TM2 that demodulates a received signal.

The image input module IIM may process the image signal and convert the processed image signal into image data that are displayed on the display module 200. The audio input module AIM may receive an external sound signal by a microphone in a recording mode, a voice recognition mode, etc., and convert the received external sound signal into electrical voice data.

The external interface IF may serve as an interface connected to an external charger, a wired/wireless data port, a card socket (e.g., a memory card, and a SIM/UIM card), or the like.

The second electronic module EM2 may include an audio output module AOM, a light emitting module LM, a light receiving module LRM, and the electronic module 500 according to an embodiment. The components may be directly mounted on the motherboard, mounted on a separate board to be electrically connected to the display module 200 through a connector or the like, or electrically connected to the first electronic module EM1.

The audio output module AOM may convert the audio data received from the wireless communication module TM or the sound data stored in the memory MM and output the converted data to the outside.

The light emitting module LM may generate and output light. The light-emitting module LM may output infrared light. The light emitting module LM may include a light-emitting diode (LED) element. The light receiving module LRM may detect infrared light. The light receiving module LRM may be activated when infrared light, which is higher than a predetermined level, are detected. The light receiving module LRM may include a complementary metal-oxide-semiconductor (CMOS) sensor. After the infrared light generated by the light emitting module LM is outputted, it is reflected by an external object (e.g., a user's finger or face), and the reflected infrared light may be incident on the light receiving module LRM. The electronic module 500 may capture an external image.

The electronic module 500 according to an embodiment may be included in at least one of the first electronic module EM1 and the second electronic module EM2. For example, the electronic module 500 may be included as one of the second electronic module EM2 together with the audio output module AOM, the light emitting module LM, and the light receiving module LRM. The electronic module 500 may detect an external subject received through the sensing area SSA, or provide a sound signal such as voice or light such as infrared light to the outside through the sensing area SSA. The electronic module 500 may capture an external subject. For example, the electronic module 500 may include a camera module and an actuator. A detailed description of the electronic module 500 will be described later.

Figure 4A:
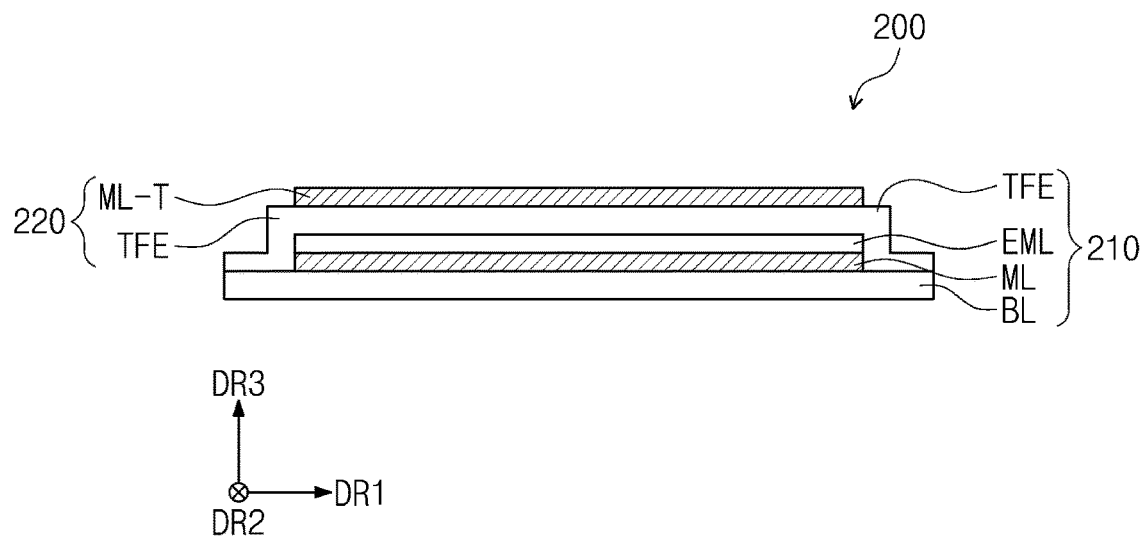
FIGS. 4A and 4B are cross-sectional views of embodiments of a display module of the electronic device of FIG. 2.
Figure 4B:
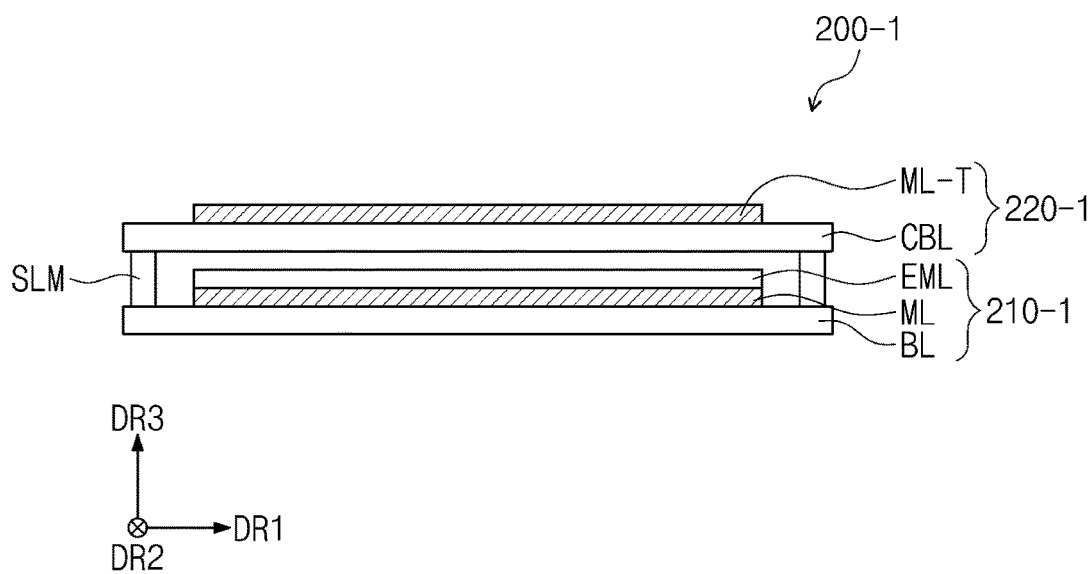

FIGS. 4A and 4B are cross-sectional views of a display module according to an embodiment.

FIG. 4A is a cross-sectional view of a display module according to an embodiment.

Referring to FIG. 4A, the display module 200 may include a display panel 210 and an input sensor 220. The display panel 210 may include a base substrate BL, a circuit element layer ML, a light emitting element layer EML, and a thin film sealing layer TFE. The input sensor 220 may include a base layer TFE and a detection circuit layer ML-T. The thin film sealing layer TFE and the base layer TFE may have the same configuration.

According to an embodiment, the display panel 210 and the input sensor 220 may be formed by a continuous process.

For example, the detection circuit layer ML-T may be formed directly on the thin film sealing layer TFE or the base layer TFE.

The base substrate BL may include a laminated structure including a silicon substrate, a plastic substrate, a glass substrate, an insulating film, or a plurality of insulating layers.

The circuit element layer ML may be disposed on the base substrate BL. The circuit element layer ML may include a plurality of insulating layers, a plurality of conductive layers, and a semiconductor layer. The plurality of conductive layers of the circuit element layer ML may constitute signal wirings or a control circuit of a pixel.

The light emitting element layer EML may be disposed on the circuit element layer ML. The light emitting element layer EML may include a light emitting layer that generates light. For example, the light emitting layer of the organic light emitting display panel may include an organic light emitting material. The light emitting layer of the quantum dot light emitting display panel may include at least one of a quantum dot and a quantum rod.

The detection circuit layer ML-T may be disposed on the base substrate BL. The detection circuit layer ML-T may include a plurality of insulating layers and a plurality of conductive layers. The plurality of conductive layers may constitute a detection electrode for detecting an external input, a detection wiring connected to the detection electrode, and a detection pad connected to the detection wiring.

FIG. 4B is a cross-sectional view of a display module according to an embodiment. In the description of FIG. 4B, the same reference numerals are used for the constituent elements described referring to FIG. 4A, and a description thereof is omitted for descriptive convenience.

Referring to FIG. 4B, the display module 200-1 may include a display panel 210-1 and an input detection unit 220-1. The display panel 210-1 may include a base substrate BL, a circuit element layer ML, and a light emitting element layer EML. The input detection unit 220-1 may include a cover substrate CBL and a detection circuit layer ML-T.

The cover substrate CBL may be disposed on the light emitting element layer EML. Each of the cover substrate CBL may include a laminated structure including a silicon substrate, a plastic substrate, a glass substrate, an insulating film, or a plurality of insulating layers. A predetermined space may be defined between the cover substrate CBL and the light emitting element layer EML. The space may be filled with air or an inert gas. In addition, in an embodiment, the space may be filled with a filler such as a silicone polymer, an epoxy resin, or an acrylic resin.

A coupling member SLM may be disposed between the base substrate BL and the cover substrate CBL. The coupling member SLM may couple the base substrate BL and the cover substrate CBL. The coupling member SLM may include an organic material such as a photocurable resin or a photoplastic resin, or may include an inorganic material such as a frit is seal, but embodiments are not limited thereto.

Figure 5:
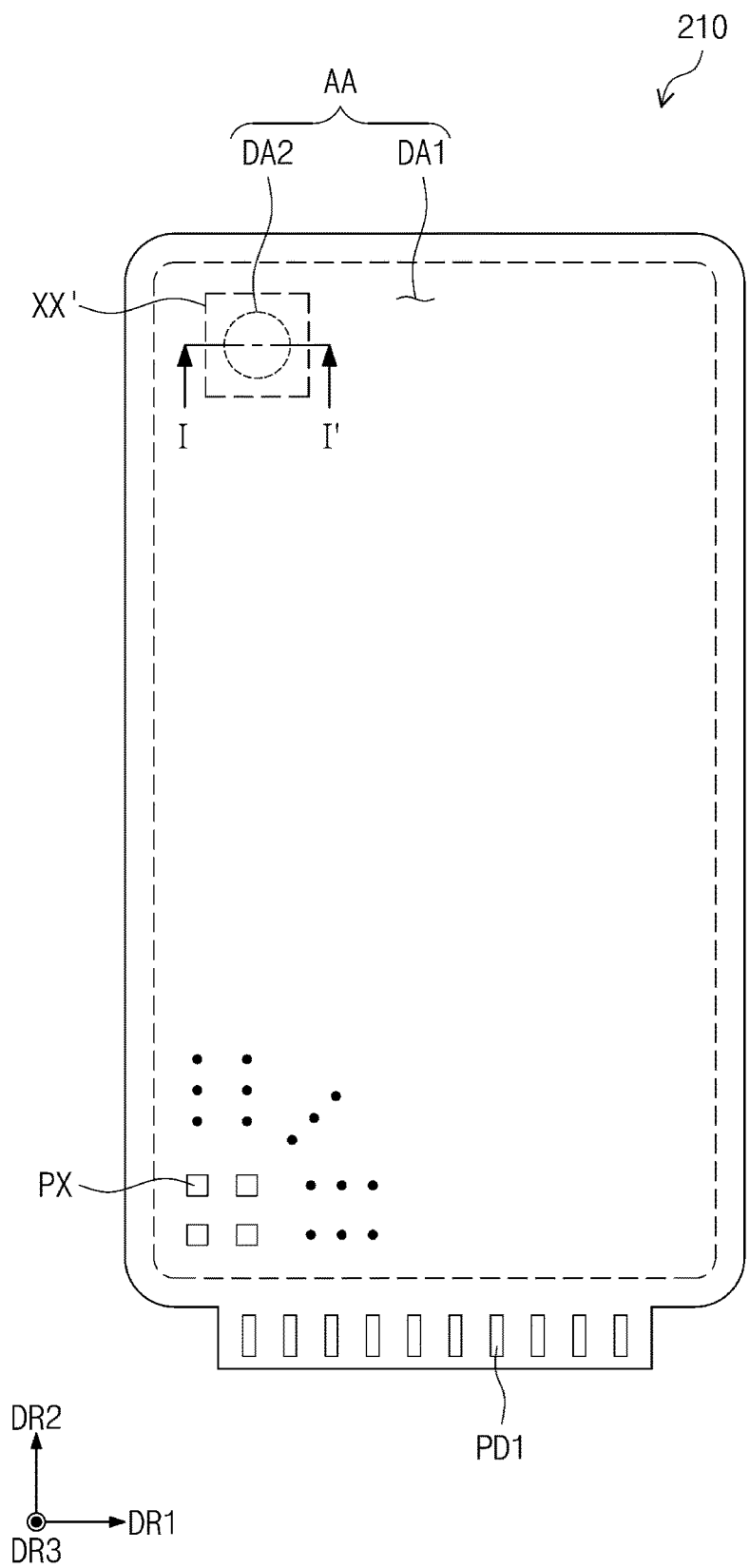
FIG. 5 is a plan view of a display panel of the electronic device of FIG. 2.

FIG. 5 is a plan view of a display panel according to an embodiment.

Referring to FIG. 5, the active area AA of the display panel 210 may correspond to the active area AA (see FIG. 2) of the display module 200 (see FIG. 2).

A plurality of pixels PX may be disposed in the active area AA. The plurality of pixels PX may be arranged along the first direction DR1 and the second direction DR2. Each of the plurality of pixels PX may display an image of one of primary colors or one of mixed colors. The primary colors may include red, green, and blue. The mixed color may include various colors such as white, yellow, cyan, and magenta. However, the color image displayed by the pixels PX is not limited thereto.

A first area DA1 and a second area DA2 may be defined in the active area AA.

An electronic module 500 (refer to FIG. 2) may be disposed under the second area DA2. The first area DA1 may have a first transmittance, and the second area DA2 may have a second transmittance. The second transmittance may be higher than the first transmittance. Accordingly, a signal may be easily transmitted to the electronic module 500 and/or received from the electronic module 500 (refer to FIG. 2) through the second area DA2. In order to increase the transmittance, a part of the second area DA2 may be omitted. For example, some of the pixels disposed in the second area DA2 may be removed.

When viewed in plane, the second area DA2 may overlap the sensing area SSA (see FIG. 2). The second area DA2 may have a larger area than the sensing area SSA (refer to FIG. 2).

In an embodiment, the first area DA1 and the second area DA2 may be defined in the active area AA. The second area DA2 may be provided to correspond to the position of the sensing area SSA (see FIG. 2). For example, the second area DA2 may overlap the sensing area SAA. Although only one second area DA2 is shown in the drawing, according to an embodiment, when the sensing areas SSA (see FIG. 2) are provided at different locations, they may be provided in plurality in correspondence thereto. The second area DA2 may be surrounded by the first area DA1.

Figure 6A:
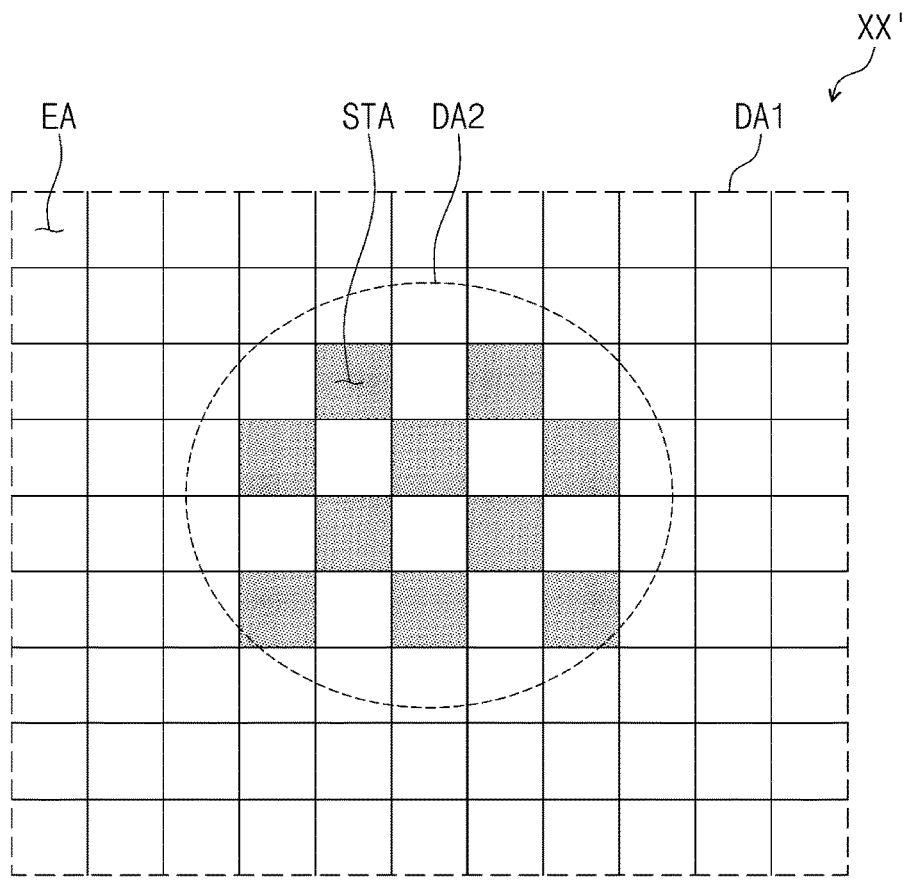
FIGS. 6A and 6B are enlarged views illustrating an area XX' of FIG. 5.
Figure 6B:
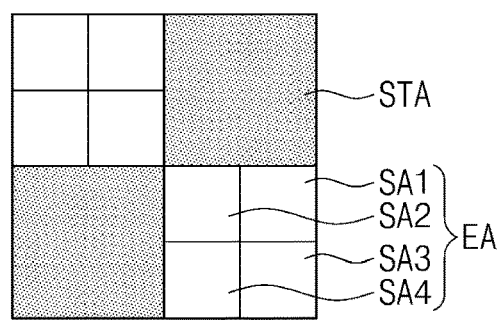

FIGS. 6A and 6B are enlarged views illustrating an area XX' of FIG. 5.

FIG. 6A is an enlarged view of XX', and FIG. 6B is an enlarged view of a part of the second area in FIG. 6A. Hereinafter, it will be described with reference to FIG. 5.

FIG. 6A is an enlarged view of a first area DA1 and a second area DA2 defined on the display panel 210. In FIG. 6A, the first area DA1 and the second area DA2 may include a plurality of light emitting areas EA. Each of the light emitting areas EA may include a plurality of pixels PX.

In an embodiment, the second area DA2 may include a plurality of signal transmission areas STA. The signal transmission areas STA may be disposed to be adjacent to the plurality of light emitting areas EA. The signal transmission areas STA may correspond to areas having higher transmittance than the light emitting areas EA. For example, in the second area DA2, the signal transmission areas STA may be areas in which pixels are not disposed, and the light emitting areas EA may be areas in which pixels are disposed.

Referring to FIG. 6B, the light emitting areas EA may include a plurality of sub light emitting areas SA1, SA2, SA3, and SA4. It is shown in the drawing that four sub light emitting areas including first, second, third, and fourth sub light emitting areas SA1, SA2, SA3, and SA4 are shown in one light emitting area EA, but embodiments are not limited thereto. For example, the number of sub light emitting areas may be smaller or larger than that.

Each of the sub light emitting areas SA1, SA2, SA3, and SA4 may include at least one of a first color light emitting area, a second color light emitting area, and a third color light emitting area. Here, the first color light emitting area may correspond to an area emitting red light, the second color light emitting area may correspond to an area emitting green light, and the third color light emitting area may correspond to an area emitting blue light. In an embodiment, each of the light emitting areas EA may include at least one first color light emitting area, two second color light emitting areas, and one third color light emitting area. For example, at least two of the first, second, third, and fourth sub light emitting areas SA1, SA2, SA3, and SA4 may each include one first color light emitting area and one second color light emitting area, and the other two of the first, second, third, and fourth sub light emitting areas SA1, SA2, SA3, and SA4 may each include one second color light emitting area and one third color light emitting area. The first, second, third, and fourth sub light emitting areas SA1, SA2, SA3, and SA4 may be freely disposed in each of the light emitting areas EA.

In an embodiment, the transmittance of the light emitting areas EA included in the second area DA2 among the light emitting areas EA may have a higher transmittance than the light emitting areas EA included in the first area DA1. For example, the density of the sub light emitting areas included in the light emitting areas EA of the first area DA1 may be greater than the density of sub light emitting areas included in the light emitting areas EA of the second area DA2.

Figure 7:
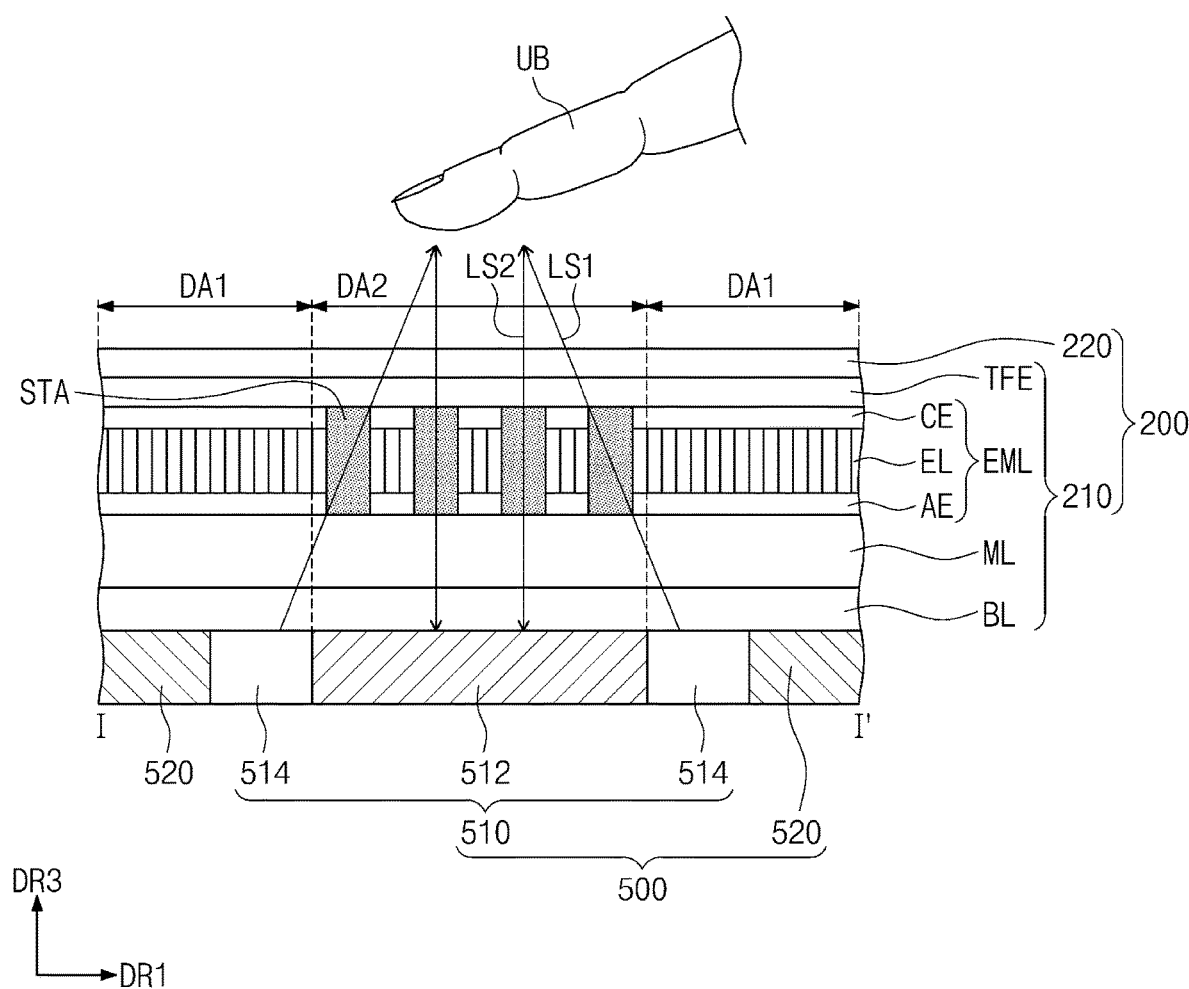
FIG. 7 is a cross-sectional view taken along line I-I' of FIG. 5.

FIG. 7 is a cross-sectional view showing a cut section taken along line I-I' of FIG. 5.

Referring to FIG. 7, the electronic module 500 is disposed under the display module 200. The electronic module 500 may be disposed under the base substrate BL of the display panel 210.

In FIG. 7, the electronic module 500 may include a first sensor 510 and a second sensor 520. Here, the first sensor 510 may be a biometric sensor that measures a user's bio-signal, and may be a photoplethysmography (PPG) sensor, but embodiments are not limited thereto. For example, the first sensor 510 may include various biometric sensors including a PPG sensor. The second sensor 520 may be a pressure sensor that measures pressure applied to an electronic device from a user.

The first sensor 510 may be a biometric sensor that measures a first signal related to biometric information such as a user's blood flow, blood pressure, oxygen saturation, and heart rate. The first sensor 510 may be disposed to overlap the second area DA2 of the display module 200. The second sensor 520 may be a pressure sensor that measures a second signal, which is a pressure signal applied from a user. The second sensor 520 may be disposed to overlap the first area DA1. The second sensor 520 may be disposed to be adjacent to the first sensor 510.

In an embodiment, the first signal measured through the first sensor 510 and the second signal measured through the second sensor 520 may be used to calculate the user's biometric information. For example, information on the user's blood pressure and the applied pressure measured through the first sensor 510 and the second sensor 520 may be used to calculate the user's blood pressure in the driving unit MCU (see FIG. 3).

The first sensor 510 may include a light emitting part 514 and a light receiving part 512. The light emitting part 514 may provide the first optical signal LS1 to the user's finger UB. The light receiving part 512 may detect the second optical signal LS2 reflected from the user's finger UB.

In an embodiment, the first optical signal LS1 and the second optical signal LS2 may pass through the signal transmission area STA of the display panel 210. For example, the first sensor 510 may measure the user's biometric information through the sensing area SSA (refer to FIG. 2) overlapping the second area DA2.

The light emitting part 514 may include at least one of an infrared light source for emitting infrared light and a red light source for emitting red light, and the light for light receiving part 512 may be a photo diode or a camera module.

Figure 8:
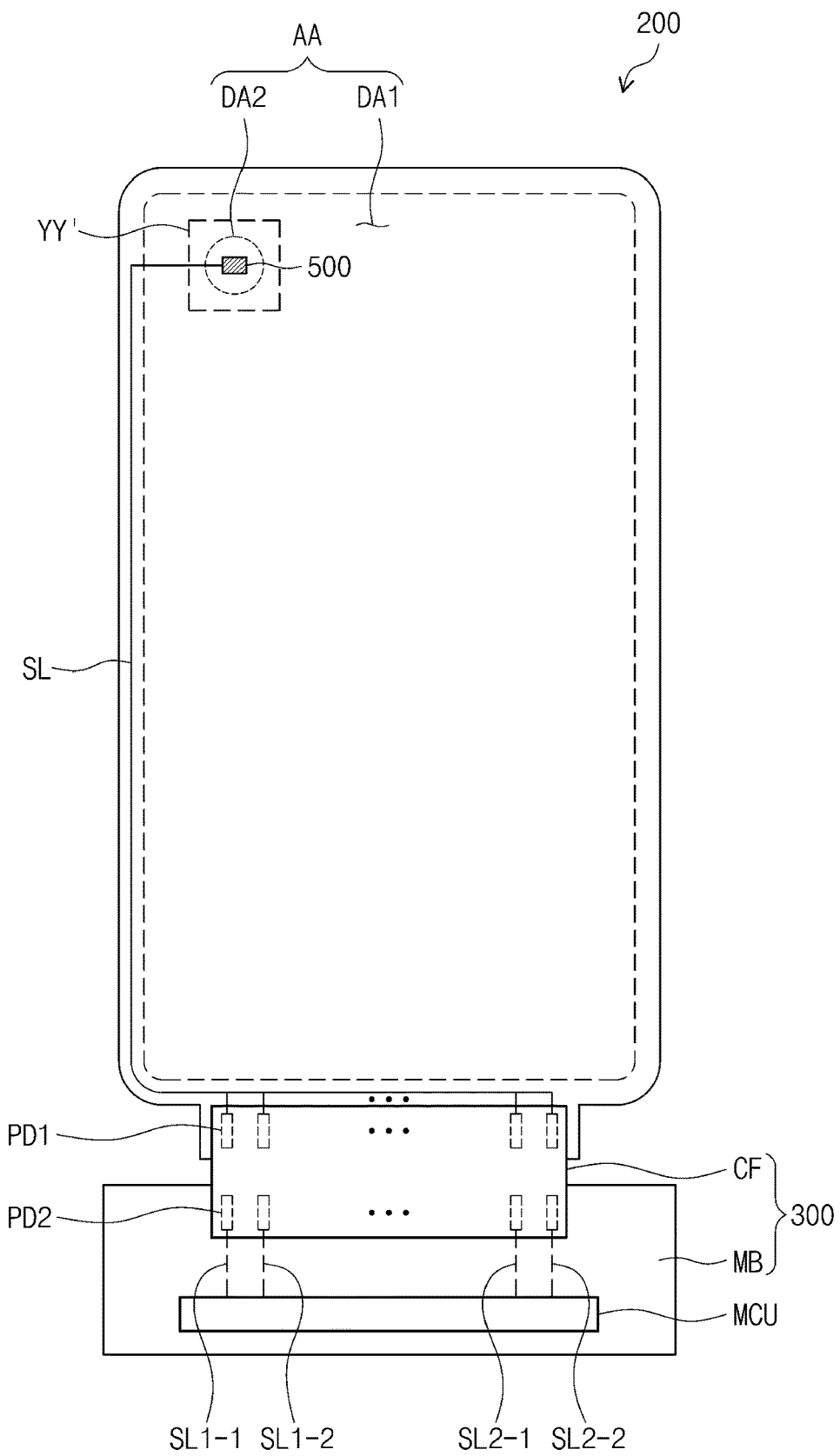
FIG. 8 is a plan view of a display module, an electronic module, and a driving circuit unit of the electronic device of FIG. 2.

FIG. 8 is a plan view of an electronic device according to an embodiment. FIG. 8 illustrates a driving circuit unit 300 electrically connected to the display module 200 according to an embodiment. Wirings electrically connecting the display module 200 and the driving circuit unit 300 are omitted.

Referring to FIG. 8, the electronic device ED (refer to FIG. 1) may include a display module 200, an electronic module 500, and a driving circuit unit 300. The electronic module 500 may be arranged to overlap the second area DA2 of the display module 200. Referring to FIG. 7, the electronic module 500 is disposed under the second area DA2 of the display module 200.

In FIG. 8, the electronic module 500 is shown briefly. The location of the electronic module 500 may be limited to FIG. 8, but the size of the electronic module 500 is not limited to FIG. 8. For example, the electronic module 500 may be out of the width of the second area DA2. The electronic module 500 may overlap the second area DA2 and a part of the first area DA1 adjacent to the second area DA2. Like the display module 200, the electronic module 500 may be electrically connected to the driving circuit unit 300.

The electronic device ED may include signal wiring SL. In an embodiment, the signal wiring SL is connected to the electronic module 500. The signal wiring SL may electrically connect the electronic module 500 and the driving circuit unit 300. In an embodiment, the signal wiring SL may electrically connect the electronic module 500 and the driving unit MCU.

The display module 200 may include a plurality of first pads PD1. The first pads PD1 may be disposed in the peripheral area NAA. The first pads PD1 may be connected to the second pads PD2 of the main circuit board MB. The first pads PD1 and the second pads PD2 are electrically connected through the flexible film CF. The flexible film CF may transmit an electrical signal generated from the main circuit board MB to the display module 200.

The signal wiring SL may be connected to the driving unit MCU through the first pads PD1 and the second pads PD2. The signal wiring SL may be provided in plurality. In an embodiment, the signal wiring SL may include a plurality of first signal wirings SL1-1 and SL1-2 and a plurality of second signal wirings SL2-1 and SL2-2. Various signals between the electronic module 500 and the driving unit MCU may be transmitted through the plurality of first signal wirings SL1-1 and SL1-2 and the plurality of second signal wirings SL2-1 and SL2-2.

The driving unit MCU may drive the electronic module 500. More specifically, the driving unit MCU may drive the display module 200 in addition to the first sensor 510 and the second sensor 520. The driving unit MCU not only drives the display module 200 but also drives the first sensor 510 and the second sensor 520 for measuring the user's biometric information, and performs various roles.

Figure 9:
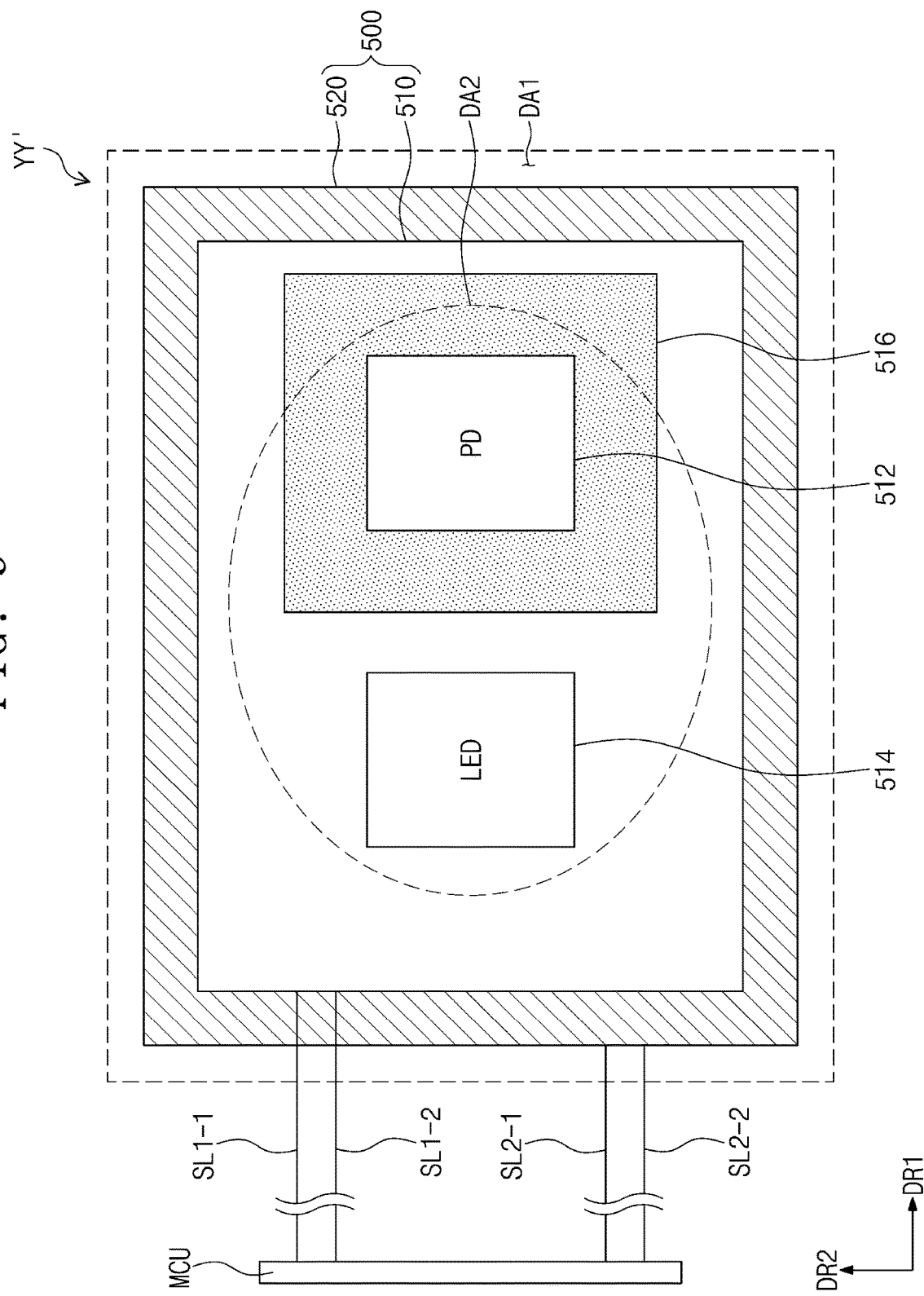
FIGS. 9, 10, and 11 are diagrams showing an enlarged area YY' of FIG. 8 illustrating embodiments of the electronic module of FIG. 8.
Figure 10:
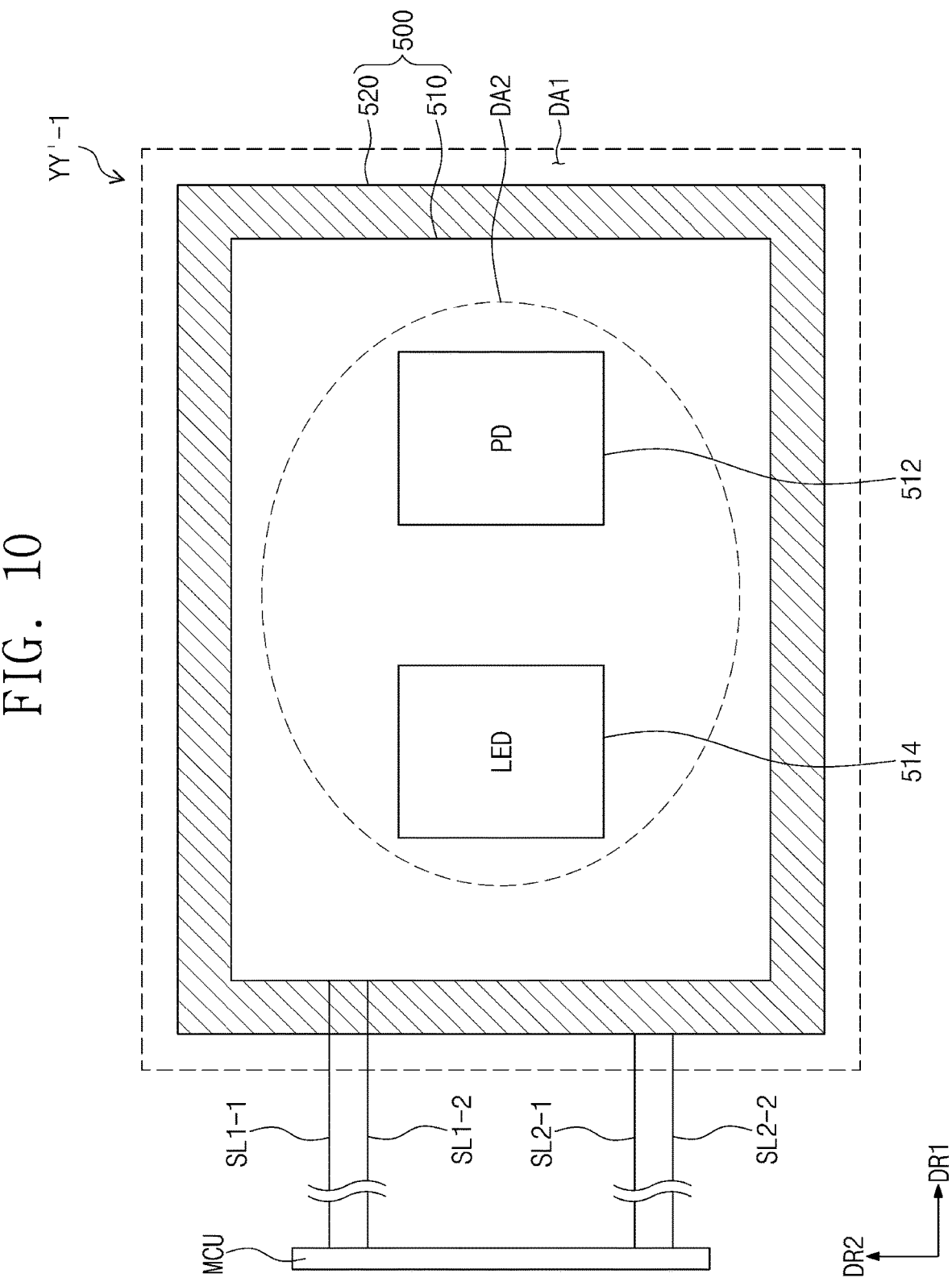
Figure 11:
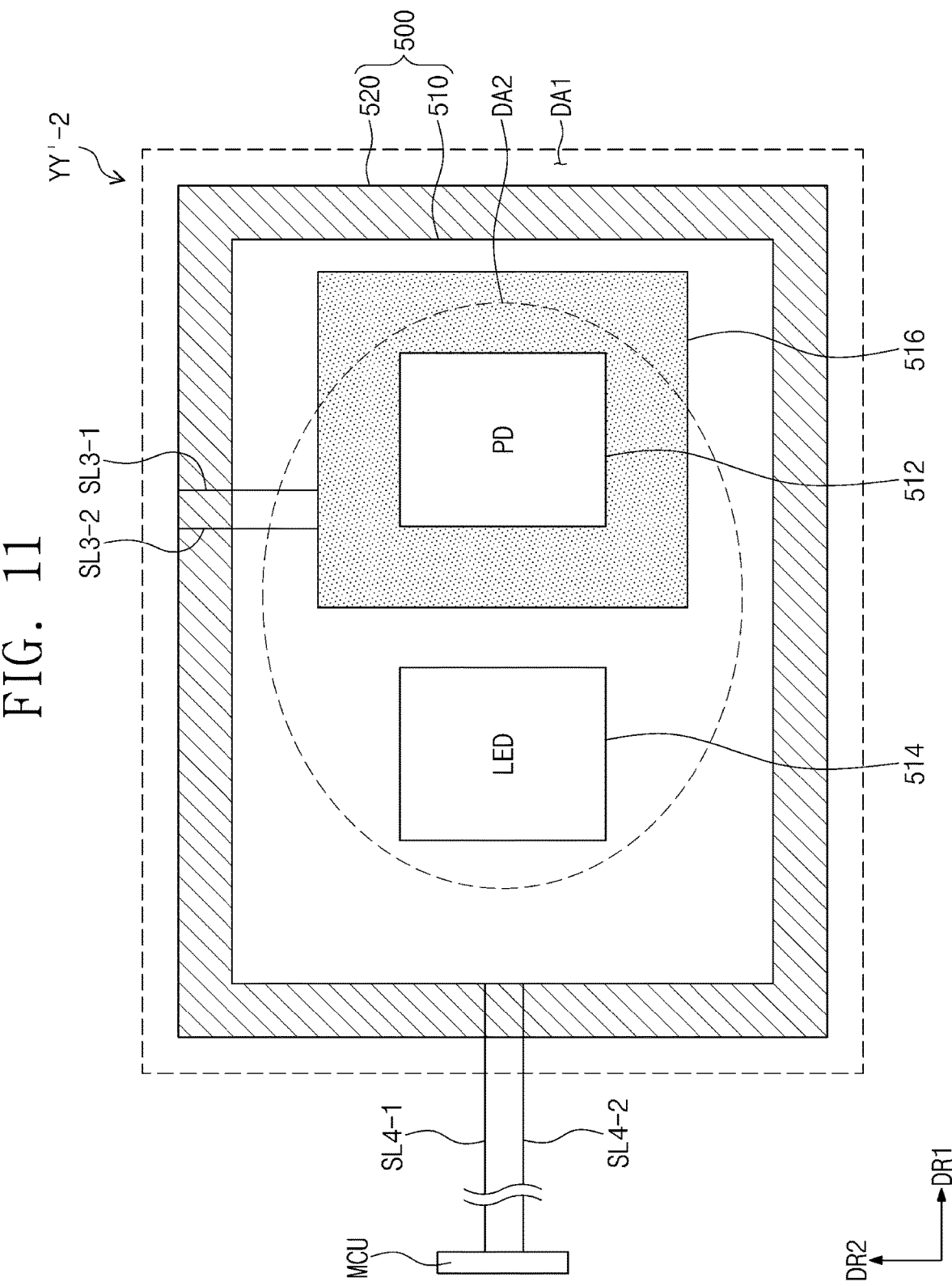

FIGS. 9, 10, and 11 are diagrams showing an enlarged area YY' of FIG. 8. FIGS. 9, 10, and 11 schematically show various forms of the electronic module 500. The area YY' may include a second area DA2 and a first area DA1 adjacent to the second area DA2.

In FIG. 9, the first sensor 510 may be disposed in the second area DA2, and the second sensor 520 may be disposed in the first area DA1.

In an embodiment, the first sensor 510 may be a biometric sensor, and the second sensor 520 may be a pressure sensor. The pressure sensor may acquire a pressure value applied to the pressure sensor and an area of a part of the user's body (e.g., a finger) in contact with the pressure sensor. A biometric sensor may measure changes in blood volume (or changes in blood flow). The driving unit MCU may calculate a user's blood pressure by receiving a pressure value from a pressure sensor and information on a change in blood volume from a biometric sensor.

The first sensor 510 may include a light emitting part 514, a light receiving part 512, and a sensor driving module 516. In an embodiment, the light emitting part 514 may include an LED, and the light receiving part 512 may include a photodiode PD. The light receiving part 512 may be disposed on the sensor driving module 516. For example, the light receiving part 512 may be embedded in the sensor driving module 516.

The sensor driving module 516 may drive the light emitting part 514 and the light receiving part 512. The sensor driving module 516 may perform control by driving the light emitting part 514 and the light receiving part 512 and electrically processing the acquired first signal. In an embodiment, the sensor driving module 516 may receive a first signal related to the user's biometric information acquired by the light emitting part 514 and the light receiving part 512, and convert the first signal into suitable electrical signals for transmission to the driving unit MCU (see FIG. 8). For example, the sensor driving module 516 may be an analog front end (AFE).

The first sensor 510 may be connected to the driving unit MCU through first signal wirings SL1-1 and SL1-2. The first signal wirings SL1-1 and SL1-2 may electrically connect the sensor driving module 516 and the driving unit MCU. The driving unit MCU may supply various commands for driving the first sensor 510 to the sensor driving module 516 through the first signal wirings SL1-1 and SL1-2. Only two of the first signal wirings SL1-1 and SL1-2 are illustrated, but embodiments are not limited thereto. For example, the number of the first signal wirings SL1-1 and SL1-2 may be more than two.

In an embodiment, the second sensor 520 may be disposed to surround the first sensor 510. The second sensor 520 may be connected to the driving unit MCU through the second signal wirings SL2-1 and SL2-2. The driving unit MCU may directly drive the second sensor 520. Two or more of the second signal wirings SL2-1 and SL2-1 may be provided including transmission/reception wiring. For example, in FIG. 9, the driving unit MCU may directly drive the second sensor 520 and may drive the first sensor 510 through the sensor driving module 516.

In FIG. 10, the first sensor 510 does not include the sensor driving module 516 (see FIG. 9). The first sensor 510 may include a light emitting part 514 and a light receiving part 512 overlapping the second area DA2 and adjacent to each other. The second sensor 520 may be disposed to be adjacent to the first sensor 510. The second sensor 520 may be disposed in an area adjacent to the second area DA2 of the first area DA1. The first sensor 510 may be connected to the driving unit MCU by the first signal lines SL1-1 and SL1-2, and the second sensor 520 may be connected to the driving unit MCU by the second signal lines SL2-1 and SL2-2.

The driving unit MCU may directly drive and control the first sensor 510 and the second sensor 520.

In FIG. 11, the first sensor 510 and the second sensor 520 may be driven by the sensor driving module 516. The second sensor 520 may be connected to the sensor driving module 516 by third signal wirings SL3-1 and SL3-2. The sensor driving module 516 may be connected to the driving unit MCU by fourth signal wirings SL4-1 and SL4-2. The driving unit MCU may drive and control the sensor driving module 516. The driving unit MCU may receive the first signal and the second signal measured by the first sensor 510 and the second sensor 520 through the sensor driving module 516 to calculate the user's biometric information.

In an embodiment, the sensor driving module 516 may alternately drive the first sensor 510 and the second sensor 520. For example, the sensor driving module 516 may alternatively drive the first sensor 510 and the second sensor 520 in a time division method. Duplicate description of FIG. 9 will be omitted.

Figure 12:
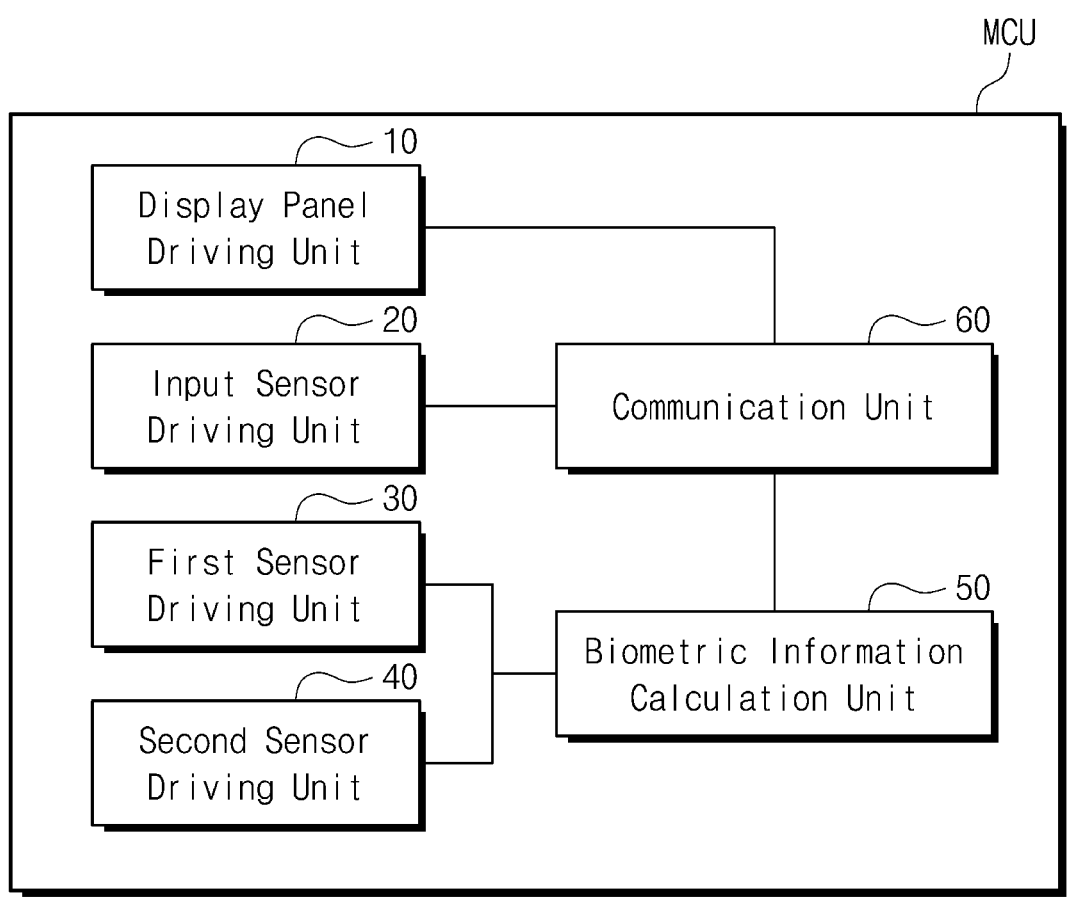
FIG. 12 is a block diagram of a driving unit of the driving circuit unit of FIG. 8.

FIG. 12 is a block diagram of a driving unit according to an embodiment.

Referring to FIG. 12, the driving unit MCU may include a display panel driving unit 10, an input sensor driving unit 20, a first sensor driving unit 30, a second sensor driving unit 40, a biometric information calculation unit 50, and a communication unit 60. For example, the driving unit MCU may drive the first sensor 510 and the second sensor 520 together with driving the display panel and the input sensor.

The display panel driving unit 10 performs a control operation for driving the display panel 210 (see FIG. 4A), and the input sensor driving unit 20 performs a control operation for driving the input sensor 220 (see FIG. 4B). The first sensor driving unit 30 may include a circuit that is connected to the first sensor 510 by the first signal wirings SL1-1 and SL1-2 to drive the first sensor 510. The second sensor driving unit 40 may include a circuit that is connected to the second sensor 520 through the second signal wirings SL2-1 and SL2-2 to is drive the second sensor 520. Unlike shown in the drawing, alternatively, the first sensor driving unit 30 and the second sensor driving unit 40 may be integrated.

The biometric information calculation unit 50 may be connected to the first sensor driving unit 30 and the second sensor driving unit 40. In an embodiment, the biometric information calculation unit 50 may receive a first signal including measurement values related to the user's biometric information from the first sensor driving unit 30, and receive a second signal including a pressure value applied from the second sensor driving unit 40. The biometric information calculation unit 50 may perform an algorithm for calculating biometric information such as a user's blood pressure based on the first signal and the second signal.

The communication unit 60 may be connected to a central processing unit of the electronic device ED (see FIG. 1). The communication unit 60 may be connected to the biometric information calculation unit 50 and provide calculated biometric information such as a user's blood pressure to the central processing unit. The communication unit 60 may be connected to the display panel driving unit 10 and the input sensor driving unit 20 and perform signal transmission between the central processing unit and the display panel and the input sensor.

An electronic device according to an embodiment includes a first sensor and a second sensor for measuring biometric information of a user, and by arranging the driving unit for driving the first sensor and the second sensor together in the driving unit of the display module, it is possible to reduce the manufacturing, design cost and design difficulty of the driving unit.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. An electronic device comprising:
a display module comprising a display panel and an input sensor disposed on the display panel, the display panel having a first area comprising a plurality of pixels and a second area having a transmittance higher than that of the first area;
a first sensor disposed below the display module, overlapping the second area, and configured to measure a first signal having biometric information of a user;
a second sensor disposed to surround the first sensor, overlapping the first area, and configured to measure a second signal applied from the user; and
a driving unit connected to the display module, the first sensor, and the second sensor, the driving unit configured to drive the first sensor and the second sensor together with the display module.

2. The electronic device of claim 1, wherein the second area of the display panel comprises a plurality of light emitting areas, and a plurality of signal transmission areas adjacent to the plurality of light emitting areas.

3. The electronic device of claim 1, further comprising a main circuit board for driving the display module,
wherein the driving unit is disposed on the main circuit board.

4. The electronic device of claim 1, wherein the driving unit comprises:
a display panel driver configured to drive the display panel;
an input sensor driver configured to drive the input sensor;
a first sensor driver configured to drive the first sensor; and
a second sensor driver configured to drive the second sensor.

5. The electronic device of claim 4, wherein the driving unit further comprises a biometric information calculator configured to calculate the biometric information of the user based on the first signal measured by the first sensor driver and the second signal measured by the second sensor driver.

6. The electronic device of claim 1, wherein the first sensor is a photoplethysmography (PPG) sensor and configured to measure at least one of a user's blood pressure, oxygen saturation, and heart rate.

7. The electronic device of claim 1, wherein the first sensor comprises a light emitter for providing light and a light receiver for detecting light reflected from the user,
wherein the light emitter comprises at least one of an infrared light source for emitting infrared light and a red light source for emitting red light,
wherein the light receiver is a photodiode or a camera module.

8. The electronic device of claim 7, wherein the first sensor comprises a sensor driving module for driving the light receiver and the light emitter.

9. The electronic device of claim 8, wherein the light receiver is formed in the sensor driving module.

10. The electronic device of claim 8, wherein the sensor driving module is connected to the driving unit, wherein the driving unit is configured to drive the first sensor through the sensor driving module, and configured to directly drive the second sensor.

11. The electronic device of claim 1, further comprising a plurality of signal wirings electrically connecting the first sensor and the second sensor to the driving unit.

12. The electronic device of claim 11, wherein the plurality of signal wirings comprise a plurality of first signal wirings electrically connected to the first sensor and a plurality of second signal wirings electrically connected to the second sensor.

13. An electronic device comprising:
a display module comprising a display panel and an input sensor disposed on the display panel, the display panel having a first area comprising a plurality of pixels and a second area having a transmittance higher than that of the first area;
a first sensor disposed below the display module, overlapping the second area, and configured to measure a first signal having biometric information of a user;
a second sensor disposed to surround the first sensor, overlapping the first area, and configured to measure a second signal applied from the user;
a sensor driving module disposed on the first sensor, connected to the second sensor, and configured to drive the first sensor and the second sensor; and
a driving unit connected to the display module and the sensor driving module, the driving unit configured to drive the display module and the sensor driving module.

14. The electronic device of claim 13, wherein the sensor driving module is configured to alternately drive the first sensor and the second sensor.

15. The electronic device of claim 13, further comprising a plurality of first signal wirings electrically connecting the second sensor to the sensor driving module.

16. The electronic device of claim 15, further comprising a plurality of second signal wirings electrically connecting the sensor driving module to the driving unit.

17. The electronic device of claim 13, wherein the sensor driving module is an analog front end for converting the first signal and the second signal into a driving signal.

18. The electronic device of claim 17, wherein the driving unit comprises a biometric information calculator configured to receive the driving signal from the sensor driving module and calculate biometric information of the user based on the driving signal.

19. The electronic device of claim 13, wherein the first sensor comprises a light emitter for providing light and a light receiver for detecting reflected light,
wherein the light emitter comprises at least one of an infrared light source for emitting infrared light and a red light source for emitting red light,
wherein the light receiver is a photodiode or a camera module.

20. The electronic device of claim 13, wherein the first sensor comprises a photoplethysmography (PPG) sensor for measuring a change in blood flow by optically detecting light reflected or transmitted from tissue and/or blood of the user, and obtaining heart rate, blood pressure, respiration, and blood oxygen saturation,
wherein the second sensor comprises a pressure sensor.

* * * * *